United States Patent [19]
D'Amelio et al.

[11] Patent Number: 5,804,206
[45] Date of Patent: Sep. 8, 1998

[54] THERAPEUTIC COMPOSITION AND METHOD FOR TREATING SKIN USING *CENTIPEDA CUNNINGHAMI* EXTRACT

[75] Inventors: Frank S. D'Amelio, Huntington; Youssef W. Mirhom, Huntington Station, both of N.Y.

[73] Assignee: Bio-Botanica, Inc., Hauppauge, N.Y.

[21] Appl. No.: 812,270

[22] Filed: Mar. 6, 1997

[51] Int. Cl.⁶ .................................................. A61K 7/48
[52] U.S. Cl. ............................ 424/401; 424/63; 424/59; 514/887
[58] Field of Search .............................. 424/401, 63, 59; 514/887

[56] References Cited

U.S. PATENT DOCUMENTS

| | | | |
|---|---|---|---|
| 4,698,360 | 10/1987 | Masquelier | 514/456 |
| 4,774,229 | 9/1988 | Jordan | 514/25 |
| 4,849,410 | 7/1989 | Jacobs et al. | 514/33 |
| 5,162,037 | 11/1992 | Whitson-Fichman | 600/12 |

FOREIGN PATENT DOCUMENTS 87102584  9/1987  China .

OTHER PUBLICATIONS

Abstract entitled "Biologically Active Constituents of *Centipeda–Minima* Sesquiterpenes of Potential Anti–Allergy Activity", Wu et al., Chem Pharm Bull (Tokyo), vol. 39, No. 12, pp. 3272–3275, 1991.

Abstract entitled "The Identification of Pyrrolizidine Alkaloid–Containing Plants, A Study on 20 Herbs of the Compositae Family", Zhao et al., Am J Chin Med, vol. 17, No. 1–2, pp. 77–78, 1989.

Abstract entitled "Phytochemical Investigation of *Centipeda–Minima*", Gupta et al., Indian J Chem Sect B Org Chem Incl Med Chem, vol. 29, No. 1, pp. 34–39, 1990.

Abstract entitled "New Distributional Records for the Flora of Maharashtra India", Karthikeyan et al., J Econ Taxon Bot, vol. 11, No. 1, pp. 60–64, 1987.

Abstract entitled "Embryological Investigations in *Centipeda–Minima* Asteraceae", Lakshmi et al., Proc Indian Acad Sci Plant Sci, vol. 96, No. 2, pp. 141–146, 1986.

Abstract entitled "Chromosome Numbers of Some Aquatic and Bank Plant Species of the Flora in the Amur River Basin USSR in Connection with the Peculiarities of its Formation", Probatova et al., Bot ZH, vol. 66, No. 11, pp. 1584–1594, 1981.

Abstract entitled "Antiprotozoal Activities of *Centipeda Minima*", Yu et al., Phytotherapy Research, vol. 8, No. 7, pp. 436–438, 1994.

Abstract entitled "Variation in the Growth of Plants of Weed Species in Dry–Seeded Rice Fields and Their Control", Ahmed et al., Proceedings, 12th Asian–Pacific Weed Science Society Conference, No. 2, pp. 465–469, 1989.

Abstract entitled "*Triterpenoid Saponins* from *Centipeda Minima*", Gupta et al., Phytochemistry, vol. 29, No. 6, pp. 1945–1950, 1990.

Abstract entitled "Weed Control in Seedling Bed of White Root (*Codonopsis Lanceolata*)", Lee et al., Research Reports of the Rural Development Admin. Upland & Industrial Crops, vol. 30, No. 2, pp. 68–73, 1988.

Abstract entitled "*Triterpenoid Saponins* from *Centipeda Minima*", Gupta et al., Phytochemistry, vol. 28, No. 4, pp. 1197–1201, 1989.

Abstract entitled "Study of COC–MAN *Centipeda Minima* L. Asteracore—An Antitussive Traditional Medicine", Pham et al., Tap Chi Duoc Hoc, Iss. 3, pp. 10–11, 1994.

(List continued on next page.)

*Primary Examiner*—Thurman K. Page
*Assistant Examiner*—D. Faulkner
*Attorney, Agent, or Firm*—Roylance,Abrams,Berdo & Goodman, L.L.P.

[57] ABSTRACT

An extract from the Centipeda genus is obtained by a successive extraction process using varying concentrations of aqueous-ethanol solvents. The resulting extract is effective in the treatment of various skin disorders including the relief of itching and dry skin from psoriasis. The extract also has antiinflammatory, antiallergetic, sunscreen and cell renewal properties.

37 Claims, 3 Drawing Sheets

OTHER PUBLICATIONS

Abstract entitled "Anti–Allergic Substances from Chinese Medicinal Plants", Sankawa et al., Adv. Chin. Med. Res., Int. Symp, pp. 171–180, 1985.

Abstract entitled "New Guaianolides from *Centipeda Minima*", Bohlmann et al., Kexue Tongbao (Foreign Lang. Ed.), vol. 29, Iss. 7, pp. 900–903, 1984.

Abstract entitled "Platelet Activating Factor (PAF) Antagonists Contained in Medicinal Plants: Lignans and Sesquiterpenes", Iwakami et al., Chem Pharm Bull (Tokyo), vol. 40, No. 5, pp. 1196–1198, May 1992.

Abstract entitled "Biologically Active Constituents of *Centipeda Minima*: Sesquiterpenes of Potential Anti–Allergy Activity", Wu et al., Chem Pharm Bull (Tokyo), vol. 39, No. 12, pp. 3272–3275, Dec. 1991.

Abstract entitled "Antimutagenic Activity of Extracts from Anticancer Drugs in Chinese Medicine", Lee et al., Mutat Res, vol. 204, No. 2, pp. 229–234, Feb. 1988.

Article entitled "Old Man Weed", Australian Aboriginal Medicine.

Abstract entitled "Occurrence of (−)–Cis–Chrysanthenyl Acetate in *Centipeda Cunninghamii*", Pinhey et al., Aust J Chem, vol. 75, No. 5, pp. 1311–1313, 1971.

Abstract entitled "Chemical Constituents of *Centipeda Minima*", Sen et al., J. Indian Chem Soc, vol. 73, No. 5, 1970.

Abstract entitled "Constituents of *Centipeda Minima*", Murakami et al., Yakugaku Zasshi, vol. 73, No. 21, 1970.

Abstract entitled "*Triterpenoid Saponins* from *Centipeda Minima*", Gupta et al., Phytochemistry, vol. 28, No. 4, pp. 1197–1202, 1989.

Abstract entitled "Study of an Australian Native Plant: *Centipeda Cunninghamii*", Wiesner, Australian Journal of Pharmacy, vol. 67, pp. 785–786, Aug. 1986.

Abstract entitled "Pharmacy of *Victorian Aborigines*", Campbell, Australian Journal of Pharmacy, vol. 54, pp. 894–900, Dec.–Jan. 1973–1974.

Abstract entitled "An Investigation into the Accuracy of Herbivore Diet Analysis", Barker, Australian Wildlife Research, vol. 13, No. 4, pp. 559–568, 1986.

THERAPEUTIC COMPOSITION AND METHOD FOR TREATING SKIN USING *CENTIPEDA CUNNINGHAMI* EXTRACT

FIELD OF THE INVENTION

The present invention is directed to a therapeutic composition containing an extract from *Centipeda cunninghami, Myriogyne cunninghami* and *Centipeda minima*. More particularly, the invention relates to a method of treating cutaneous disorders using a composition containing an extract from *Centipeda cunninghami, Myriogyne cunninghami* and *Centipeda minima*.

BACKGROUND OF THE INVENTION

The plant kingdom has been a rich source for medicinal preparations used to treat a variety of illnesses in animals and particularly in man. The plants or certain parts of the plant are usually used to make teas or other preparations which can be taken orally. Many plants are used to prepare compositions for applying topically to the skin.

One example of a plant having been used for medicinal purposes is *Centipeda cunninghami*. This plant, also known as common sneezeweed, old man weed, scentwood, Gukwonderuk or koona puturku has been used internally by the Aboriginal people of Australia for various ailments.

The plant is known to grow primarily in Victoria Australia along the banks of streams and in the back washes of rivers or streams where the water is stagnant. The plant is only known to grow in the lower temperate regions of Australia.

*Centipeda cunninghami* has been traditionally used by boiling the plant in water to produce a tea. The tea is often taken orally to treat illnesses including, for example, tuberculosis. Other known uses of the tea solution or decoction include the treatment of purulent ophthalmia and sandy blight and for alleviating eye inflammation by bathing the eyes with a cooled solution. Other uses of the plant have been to place the plant around the head of the person for the relief of colds. It has also been administered as antiprotozoal.

Although *Centipeda cunninghami* has been known and used by the Aboriginal people, little or no documentation exists reporting the illnesses being treated. The documents that identify various medicinal uses of the plant provide no information to support the asserted effectiveness of the plant.

The active component of *Centipeda cunninghami* responsible for the medicinal properties is also unknown. The prior solutions are known to contain a volatile oil having a bitter principle of myriogenin and cis-chrysanthenyl acetate.

These prior uses of *Centipeda cunninghami* have not been shown to be entirely effective for treating many illnesses, moreover, topical application has not been explored. Accordingly, there is a continuing need for a rational effective use of *Centipeda cunninghami* and related plants.

SUMMARY OF THE INVENTION

The present invention is directed to a preparation and composition containing an extract from the plant genus Centipeda and to a method of obtaining the extract. The extract has been found effective in treating various illnesses specifically cutaneous disorders in humans. Accordingly, a primary object of the invention is to provide an extract from the plant genus Centipeda for use in topical applications and oral preparations for treating various illnesses.

A further object of the invention is to provide an extraction procedure for extracting substantially most of the active compounds from the plant genus Centipeda to obtain a holistically balanced extract.

Still another object of the invention is to provide a method for treating skin disorders by applying an effective amount of a composition containing a standardized holistically balanced extract from the plant genus Centipeda.

A further object of the invention is to provide a process of extracting constituents from the Centipeda plant which is efficient and economical.

Another object of the invention is to provide a method of obtaining a plant extract by a sequential extraction utilizing various concentrations of ethanol in water.

The objects of the invention are basically attained by providing a process for obtaining a plant extract comprising the steps of providing a plant material of the Centipeda genus in a coarse powder, sequentially contacting and extracting said plant material with a plurality of ethanol in water solvents and obtaining an extract solution of each of said solvents wherein each sequential extraction solvent has a different ethanol concentration and said solvents having an ethanol concentration ranging from about 20% by volume to about 80% by volume, and combining said extract solutions to obtain a plant extract.

The objects of the invention are also basically attained by providing a holistically balanced extract of Centipeda, wherein said extract is produced by the process comprising the steps of providing a Centipeda plant material in coarse powder, sequentially contacting and extracting said plant material with a plurality of ethanolic solvents and obtaining a plurality of extract solutions wherein each of said ethanolic solvents has a different ethanol concentration, and have an ethanol concentration ranging from about 80% by volume to about 20% by volume, and combining said extract solutions to obtain said holistically balanced extract, and adding an effective amount of glycerol to prevent precipitation of compounds from solution.

The objects of the invention are basically attained by providing an effective preparation for topically treating skin disorders containing an appropriate amount of a holistically balanced extract from Centipeda in a suitable vehicle.

The objects of the invention are basically attained by providing a process for the relief of itching caused by skin disorders, a process for treating inflammation, a process for promoting cell renewal, and a process of protecting the skin from sun exposure comprising the step of topically applying a pharmacologically effective amount of a composition to a skin area in need of treatment, wherein said composition comprises a holistically balanced extract of Centipeda.

These objects of the invention and other unique features of the invention will be apparent to one skilled in the art from the following detailed description of the invention.

BRIEF DESCRIPTION OF THE DRAWINGS

Referring the drawings which form a part of this disclosure in which.

DETAILED DESCRIPTION OF THE INVENTION

Figure 1:
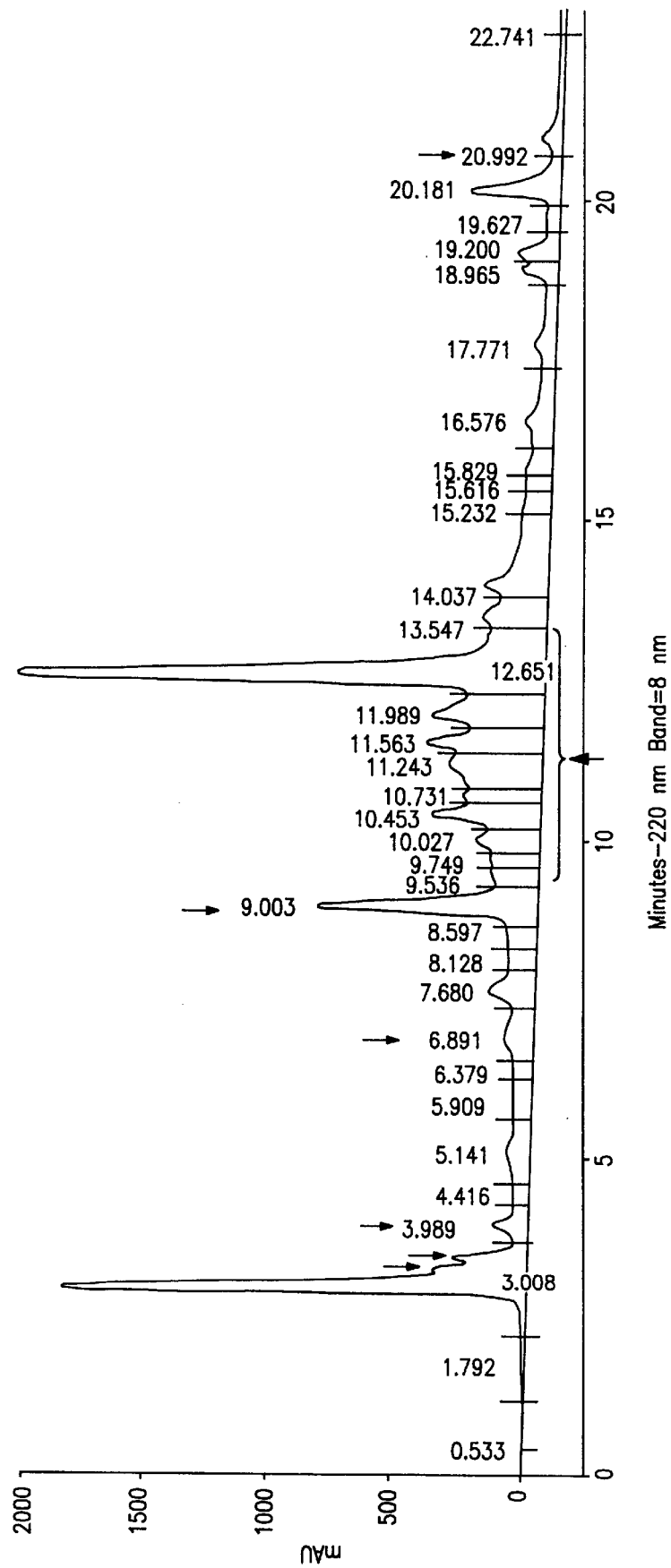
FIG. 1 is chromatogram of the extract obtained by a preferred embodiment of the invention.

The present invention is directed to an extract prepared from the plant genus Centipeda and to a process for preparing the extracts. The invention is further directed to medicinal preparations and compositions containing the extract as the active component and to a method of treating various illnesses and disorders using the medicinal preparations containing an effective amount of the extract.

The extract of the present invention in preferred embodiments is a holistic balance of the various and numerous compounds that occur naturally in the plant. As used herein, the term "holistic" refers to the extract having substantially all of the soluble compounds and complexes that can be extracted from the plant in substantially the same proportions as originally present in the plant.

The plants used in the present invention are of the Centipeda genus. The preferred plant is *Centipeda cunninghami* A.Br. & Aschers, hereinafter referred to as *Centipeda cunninghami*, which is only known to grow naturally in the temperate regions of Australia, along river and stream banks and in back washes of standing water. The mature plant is an aromatic perennial herb that appears glabrous. However, the young shoots are typically quite woolly. *Centipeda cunninghami* is a herbaceous plant up to about 30 cm high. Stem is green, cylindrical, longitudinally striated with short internodes; leaves (1–3 cm) are green, simple sessile, alternate, oblong-ovate, margin, denate, apex acute, venation, pinnate reticulate, midrib conspicuous, prominent on the lower side; odor is characteristic, aromatic, sterutatory; taste is aromatic, slightly bitter. The flower heads (0.5–0.8 cm in diameter) which grow during the warmer months are sessile.

*Centipeda cunninghami* is also known by a number of common or vernacular names, including common sneezeweed, scentwood, old man weed and Gukwonderuk. The plant was traditionally used in Aboriginal medicine in the form of a decoction by heating or boiling the plant in water to make a dark liquor which is then allowed to cool.

Although *Centipeda cunninghami* is the generally preferred plant, other species of the Centipeda genus can also be used. Other species which can be used include, for example, *Centipeda minima* (spreading sneezeweed, also known as *C. orbicularis*) and *C. thespidioides* known as Desert Sneezeweed.

The various compounds and constituents of *Centipeda cunninghami* are complex and not well documented. The compounds known from the literature include myriogenin and cis-chrynanthenyl acetate. The compounds of *Centipeda minima* are reported to contain isobutyroylplenolin, senecioylplenolin, lupeol acetate, hexacosanol, B-sitosterol, stigmasterol, taraxasteryl palmitate, taraxasteryl acetate, taraxasterol, stigmasterol, arnidol, 10-isobutyryl-oxy-8,9-epoxythymol isobutyrate, 9,10-diisobutyryloxy-8-hydroxythymol, arnicolide, c. breviofolin, helenanin, florilenalin isobutyrate, florilenalin isovalerate and florilenalin angelate.

The plants selected for preparing the extract of the invention are preferably collected and harvested at the time and stage of growth when the volatile compounds in the plant are at their peak. Typically, it is preferred to harvest the plant at the flowering stage. In addition, it is preferable that the plants are harvested in the early morning hours before plants are exposed to direct sunlight since this is the time of day when the volatile components of the plant are at the highest concentration. The heat from direct sunlight volatizes some of the volatile compounds and the sunlight itself decomposes some compounds such that the concentration of some compounds decrease throughout the course of the day.

The entire plant is harvested for extraction. The freshly harvested plants can be extracted immediately without further processing. Typically, it is desirable to dry the harvested plant material for storage until needed. In preferred embodiments, the plant material is dried at room temperature and at atmospheric pressure to minimize loss of volatile compounds in the plant material and particularly is dried in the absence of direct sunlight.

The harvested plant is preferably ground, cut or pulverized to reduce the particle size of the plant material prior to extraction. In preferred embodiments, the plant material is dried and reduced to about 4 mesh to provide efficient extraction of the soluble compounds contained in the plant.

Typically, the particle size of the plant material is reduced to a sufficiently small size to promote efficient contact with the solvent and to extract the soluble compounds. However, it is desirable to avoid reducing the particle size to such a small size that the plant material remains in suspension in the solvent and cannot be easily separated by filtration. For example, it is desirable to avoid a small particle size which requires centrifugation to efficiently recover the solvent and its solutes since this increases the costs and labor of the separation process. In a similar manner a large particle size is to be avoided since this increases the volume of solvent required and the length of time to effectively extract the soluble compounds.

The plant extract of the invention can be obtained using suitable solvents including polar, non-polar, semipolar solvents and mixtures thereof. Suitable polar solvents include lower alkyl alcohols, lower alkyl ethers and lower alkyl ketones and aldehydes. In preferred embodiments as discussed hereinafter in greater detail the solvent system is aqueous-ethanol of varying concentrations. Preferred embodiments of the invention avoid the presence of toxic solvents in the extraction process.

Typically, the plant yields about 23% to 28% solids on dry weight basis. The extract of the invention can be prepared by a number of extraction procedures. Suitable procedures include, for example, maceration, percolation, extraction using supercritical fluids, liquefied gases or various suitable solvents.

In preferred embodiments, the extraction procedure produces a holistically balanced extract having substantially all of the ethanol-soluble and aqueous-ethanol-extractable constituents and compounds present in substantially the same proportions as present in the plant. A preferred extraction procedure is a multi-step, successive maceration and percolation process using a number of aqueous-ethanol solvents having varying concentrations of ethanol in water. The extraction is preferably carried out at room temperature. The plant material is ground or powdered and percolated successively with aqueous-ethanol mixtures containing, for example, 80%, 70%, 60%, 50%, 40%, 30% and 20% by weight ethanol. The plant material is percolated with each solvent mixture in this sequence of highest ethanol concentration to the lowest ethanol concentration and in the amount of about 3.0 ml to 7.0 ml per gram and preferably about 5.0 ml per gram of the plant material.

The recovered ethanolic solvents containing the soluble constituents of the plant are combined to produce a single extract solution. The solvent can be removed by conventional procedures at low temperature (preferably less than 60° C.) under reduced pressure to reduce the volume and increase the concentration of the extracted compounds. The evaporation or concentration process used is preferably selected and carried out under conditions to minimize loss of the volatile compounds, efficient cooling being mandatory.

The resulting extract from *Centipeda cunninghami* typically contains not less than 0.2% by weight of sequiterpene lactones calculated as Brevilin A. The extract, as determined by HPLC, contains Brevilin A, Arnicolide, Arnicolide B, Arnicolide C, Caryophyllane-2, 6-Beta-oxide, Florilenalin-angelate, Florilenalin-isobutyrate, Florilenalin-isovalerate, Helenalin, Microhelenalin B, Plenolin, 6-0-angeloyl, Plenolin, 6-0-senecoyl, Plenolin, isobutyroyl, Aurantiamide acetate, Apigenin, (cis) Chrysanthenyl acetate, Kaempferol-7-glucosyl-rhamnoside, Lupeol acetate, Quercetin, Scoparol, Beta-sitosterol, Taraxasterol, Thymol, 10-Isobutyryl-oxy-8, 9-epoxy-isobutyrate, and 9-epi Hardwickiic acid.

A preferred percolation extraction process uses successive stages with different solvents of varying ethanol concentrations. The plant material to be processed is generally dried and ground. Preferably, the plant material is reduced to at least 4 mesh. The extraction is carried out by placing the powdered plant material in a vessel and mixing with a sufficient amount of 80% aqueous ethanol to cover the material. The mixture of the plant material and the 80% ethanol are covered and allowed to stand at room temperature to absorb the menstruum, soften the plant material and dissolve a portion of the ethanol soluble components. The material is then transferred to a percolator fitted with a screen to prevent the plant material from passing through. With the valve closed, the 80% aqueous ethanol is added to the percolator to fill the percolator to completely cover the plant material. Generally, the plant material is covered with about two inches of the 80% aqueous-ethanol to ensure the plant material is completely saturated.

The percolator is then covered and the plant material allowed to macerate for sufficient time to dissolve the soluble components. Generally, the plant material is allowed to percolate for about 12–24 hours at room temperature and preferably for at least about 18 hours. The solvent is then allowed to percolate into a collection vessel while adding an amount of the solvent to the percolator to extract substantially all of the soluble compounds which can be extracted by the 80% aqueous ethanol. In preferred embodiments, the amount of the 80% aqueous-ethanol is about 4–6 ml per gram of plant material and preferably about 5 ml per gram of plant material. The solvent is preferably percolated and collected at a rate of about 10 mls/minute for a 500 gram sample of the plant material.

The percolating step is then repeated using 60% aqueous ethanol, 40% aqueous ethanol and finally 20% aqueous ethanol following the above process. The percolates are combined in a single vessel and an amount of glycerol is added to prevent precipitation of the extracted solutes. The mixture is then filtered to remove any of the plant material and to recover the extract. The yield of the extract by this method is about 23% to about 28% by weight based on the dry weight of the plant material. The extract is preferably filtered through a Whatman No. 1 filter or equivalent filtration material to remove any solids.

The resulting extract obtained from this process is a holistically balanced composition comprising Brevilin A, Arnicolide, Arnicolide B, Arnicolide C, Caryophyllane-2, 6-Beta-oxide, Florilenalin-angelate, Florilenalin-isobutyrate, Florilenalin-isovalerate, Helenalin, Microhelenalin B, Plenolin, 6-0-angeloyl, Plenolin, 6-0-senecoyl, Plenolin, isobutyroyl, Aurantiamide acetate, Apigenin, (cis) Chrysanthenyl acetate, Kaempferol-7-glucosy-rhamnoside, Lupeol acetate, Quercetin, Scoparol, Beta-sitosterol, Taraxasterol, Thymol, 10-Isobutyryl-oxy-8, 9-epoxy-isobutyrate, and 9-epi Hardwiic acid.

In preferred embodiments, an amount of glycerol is added to the extract. It has been found that glycerol prevents several of the slightly soluble compounds, such as phlobaphenes, from precipitating during storage thereby serving as an effective preservative.

The composition of the resulting ethanolic extract has a large number of compounds in varying amounts. The ethanolic extract can be assayed using HPLC for total sesquiterpene lactones as "Brevilin A". An example of a suitable device is a Shimadzu LC-10A liquid chromatograph fitted with a C18 column. The suitable solvent system can be 80% acetonitrile and 20 by volume water containing 0.1% phosphoric acid by weight. The flow rate is preferably about 1.0 ml/minute and the UV detector set to 220 nm. The extract is initially diluted with methanol-water (1:1).

The extraction process is preferably carried using a sufficient volume of solvent system and over a period of time to extract substantially all of the soluble compounds in the plant material. In the preferred embodiments, the final extract contains substantially all of the aqueous-ethanol soluble compounds.

The extract has been found to be effective for topically treating various skin disorders including eczema, psoriasis, acne, herpes, bed sores, puritis and various allergic reactions. The extract can be used directly or combined with a vehicle for topical application. The vehicle can be any suitable vehicle as known in the art. The extract can be admixed with a cream, lotion, ointment, nebulizer, hair or scalp preparation as a vehicle where the extract is present in the amount of about 1.0% to 5.0% by weight and preferably about 2.0% to about 3.0% by weight. The extract is also found to be an effective antiinflammatory composition, antifungal composition, UV blocking or sun screen composition and for promoting cell renewal as a healing agent. The topical antiinflammatory (antihistaminic, antiallergic), sunscreen, and cell renewal properties have definitely been proved clinically and a significant difference ($P<0.005$) was obtained.

The extract is preferably diluted with 20% ethanol to obtain a final concentration of 0.2% sesquiterpene lactones calculated as Brevilin A. The extract further contains about 3% by volume glycerol. The extract can be applied topically to the skin or combined with other standard components used in preparing lotions or creams.

The following non-limiting examples disclose various embodiments of the invention.

Example 1

Mature *Centipeda cunninghami* was collected during the flowering stage before being exposed to direct sunlight. The plant material was then dried for several hours in the absence of direct sunlight. The dried plant material was ground to a powder of about #4 mesh.

500 gms of the powdered plant material was placed in vessel and the mixed with a sufficient amount of 80% aqueous ethanol to completely cover the plant material. The vessel was covered with a lid and allowed to stand for about 30 minutes until the ethanol was absorbed by the plant material. The dampened plant material was transferred to a 5 liter percolator fitted with a screen to collect the ground plant material. With the valve of the percolator closed, an amount of 80% ethanol was added to the percolator to about 2 inches above the plant material. The percolator was covered with a lid to prevent evaporation of the solvent and the plant material allowed to macerate for 18 hours at room temperature of about 23°–27° C. At the end of the maceration, the valve was opened and the extract collected in a 3 gallon vessel at a rate of about 10 ml per minute. As the ethanol was drained, additional 80% ethanol was added and allowed to percolate until a total of 2500 ml was collected.

2500 ml of 60% aqueous ethanol was then percolated through the plant material at a rate of 10 ml per minute. The 60% ethanol was collected in the same container with the 80% ethanol. Thereafter 2500 ml of 40% aqueous ethanol was percolated through the plant material and collected in the vessel. Finally, 2200 ml of 20% ethanol was percolated through the plant material and collected in the vessel with the previously collected solvents. 300 grams (238 mls) of 99.5% glycerol was added to the solvent and blended thoroughly. Thereafter the mixture was filtered through a Whatman #1 filter paper to remove any solids.

The collected product was assayed using a Shimadzu LC-10A liquid chromatograph fitted with a C18 column for total sesquiterpene lactones as Brevilin A. The sample was diluted with methanol-water (1:1) using standard dilution procedures for liquid chromatography. The solvent system used was 80% by volume acetonitrile and 20% by volume water containing 0.1% by weight phosphoric acid. The flow rate was adjusted to 1.0 ml per minute and a UV-detector set at 220 nm. The chromatography data showed a composition of Brevilin A, Arnicolide, Arnicolide B, Arnicolide C, Caryophyllane-2, 6-Beta-oxide, Florilenalin-angelate, Florilenalin-isobutyrate, Florilenalin-isovalerate, Helenalin, Microhelenalin B, Plenolin, 6-0-angeloyl, Plenolin, 6-0-senecoyl, Plenolin, isobutyroyl, Aurantiamide acetate, Apigenin, (cis) Chrysanthenyl acetate, Kaempferol-7-glucosyl-rhamnoside, Lupeol acetate, Quercetin, Scoparol, Beta-sitosterol, Taraxasterol, Thymol, 10-Isobutyryl-oxy-8, 9-epoxy-isobutyrate, and 9-epi Hardwickiic acid.

The HPLC chromatogram is shown in FIG. 1 and the numerical data is shown in Table 1.

TABLE 1

| Peak # | RT | AREA | AREA % | HEIGHT |
|---|---|---|---|---|
| — | 0.470 | 0 | 0.00 | 0 |
| 1 | 0.533 | 148538 | 0.07 | 918 |
| 2 | 1.792 | 681917 | 0.31 | 12918 |
| 3 | 3.008 | 30098522 | 13.50 | 1854215 |
| 4 | 3.989 | 2749201 | 1.23 | 136989 |
| 5 | 4.416 | 1086853 | 0.49 | 56571 |
| 6 | 5.141 | 4368787 | 1.96 | 86632 |
| 7 | 5.909 | 2475230 | 1.11 | 67348 |
| 8 | 6.379 | 1242468 | 0.56 | 69451 |
| 9 | 6.891 | 4626306 | 2.08 | 111872 |
| 10 | 7.680 | 4381785 | 1.97 | 179241 |
| 11 | 8.128 | 2061792 | 0.92 | 101685 |
| 12 | 8.597 | 2208741 | 0.99 | 111465 |
| 13 | 9.003 | 14472663 | 6.49 | 865658 |
| 14 | 9.536 | 3377091 | 1.52 | 184284 |
| 15 | 9.749 | 2105757 | 0.94 | 185971 |
| 16 | 10.027 | 4933426 | 2.21 | 245881 |
| 17 | 10.453 | 7557192 | 3.39 | 425889 |
| 18 | 10.731 | 4083164 | 1.83 | 301805 |
| 19 | 11.243 | 10793563 | 4.84 | 363888 |
| 20 | 11.563 | 8277579 | 3.71 | 449526 |
| 21 | 11.989 | 11195767 | 5.02 | 441452 |
| 22 | 12.651 | 47129008 | 21.14 | 2444159 |
| 23 | 13.547 | 6247085 | 2.80 | 254307 |
| 24 | 14.037 | 11364578 | 5.10 | 247088 |
| 25 | 15.232 | 2050137 | 0.92 | 104903 |
| 26 | 15.616 | 1358132 | 0.61 | 98714 |
| 27 | 15.829 | 2341923 | 1.05 | 101036 |
| 28 | 16.576 | 5312008 | 2.38 | 108359 |
| 29 | 17.771 | 3841035 | 1.72 | 80086 |
| 30 | 18.965 | 1985999 | 0.89 | 139737 |
| 31 | 19.200 | 2730631 | 1.22 | 159926 |
| 32 | 19.627 | 1211965 | 0.54 | 51873 |

TABLE 1-continued

| Peak # | RT | AREA | AREA % | HEIGHT |
|---|---|---|---|---|
| 33 | 20.181 | 6217850 | 2.79 | 349223 |
| 34 | 20.992 | 3447791 | 1.55 | 81353 |
| 35 | 22.741 | 557576 | 0.25 | 20559 |
| 36 | 23.488 | 1759372 | 0.79 | 67180 |
| 37 | 24.533 | 300265 | 0.13 | 17252 |
| 38 | 24.789 | 343275 | 0.15 | 16056 |
| 39 | 25.216 | 759457 | 0.34 | 11275 |
| 40 | 29.461 | 1024243 | 0.46 | 24750 |

The HPLC data demonstrate that at least 40 identifiable compounds are present in the extract prepared by the above process.

Example 2

Figure 2:
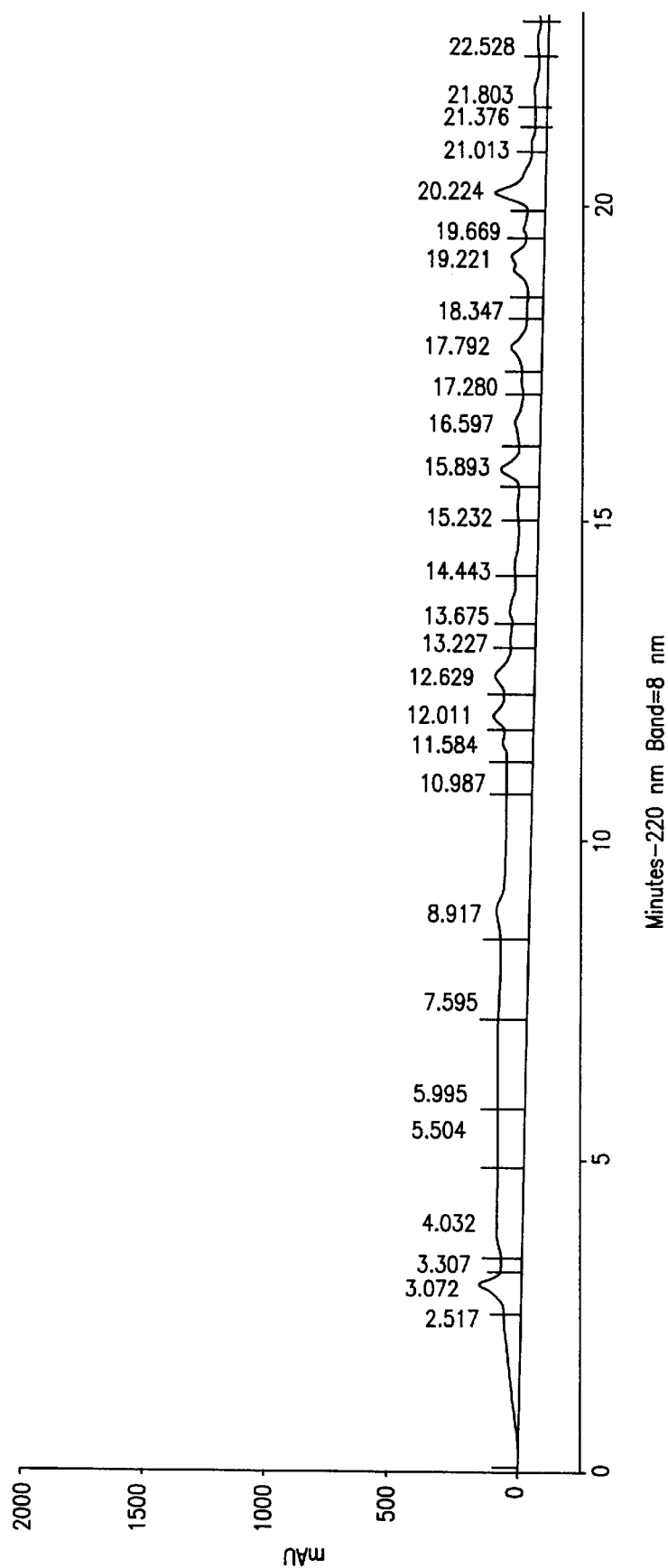
FIG. 2 is a chromatogram of the extract obtained using a 95% aqueous ethanol solvent.

An extract was prepared from *Centipeda cunninghami* following the process of Example 1 except that the extraction was carried out using only 95% aqueous ethanol. The resulting extract was assayed using HPLC. The chromatography results are shown below in Table 2 and in the chromatogram of FIG. 2.

TABLE 2

Channel A Results - PDA Channel 1, 220 nm, 8 nm Band

| Peak # | RT | AREA | AREA % | HEIGHT |
|---|---|---|---|---|
| — | 0.470 | 0 | 0.00 | 0 |
| 1 | 2.517 | 6085965 | 4.25 | 79689 |
| 2 | 3.072 | 4769300 | 3.33 | 189226 |
| 3 | 3.307 | 1242795 | 0.87 | 98900 |
| 4 | 4.032 | 9993022 | 6.98 | 119967 |
| 5 | 5.504 | 6456680 | 4.51 | 121159 |
| 6 | 5.995 | 10762121 | 7.51 | 123409 |
| 7 | 7.595 | 9629010 | 6.72 | 132119 |
| 8 | 8.917 | 16913738 | 11.81 | 141148 |
| 9 | 10.987 | 3272280 | 2.28 | 117137 |
| 10 | 11.584 | 3621662 | 2.53 | 133161 |
| 11 | 12.011 | 4897081 | 3.42 | 172942 |
| 12 | 12.629 | 5909683 | 4.13 | 166264 |
| 13 | 13.227 | 2497032 | 1.74 | 110785 |
| 14 | 13.675 | 4841784 | 3.38 | 117804 |
| 15 | 14.443 | 4958465 | 3.46 | 100103 |
| 16 | 15.232 | 2748492 | 1.92 | 91642 |
| 17 | 15.893 | 4302001 | 3.00 | 160637 |
| 18 | 16.597 | 4639429 | 3.24 | 108948 |
| 19 | 17.280 | 1749180 | 1.22 | 82494 |
| 20 | 17.792 | 4597911 | 3.21 | 133933 |
| 21 | 18.347 | 1473608 | 1.03 | 69117 |
| 22 | 19.221 | 5478896 | 3.83 | 138827 |
| 23 | 19.669 | 2010293 | 1.40 | 88323 |
| 24 | 20.224 | 6252913 | 4.37 | 210509 |
| 25 | 21.013 | 1339653 | 0.94 | 64636 |
| 26 | 21.376 | 898147 | 0.63 | 51444 |
| 27 | 21.803 | 2211746 | 1.54 | 53018 |
| 28 | 22.528 | 1287997 | 0.90 | 45608 |
| 29 | 23.061 | 624919 | 0.44 | 35944 |
| 30 | 23.509 | 2526940 | 1.76 | 98806 |
| 31 | 24.128 | 1070923 | 0.75 | 51497 |
| 32 | 24.533 | 3105068 | 2.17 | 46102 |
| 33 | 29.483 | 1058372 | 0.74 | 24838 |

This data when compared with the data of Example 1 demonstrate that the extraction process of Example 1 using a series of extraction steps with varying solvent concentrations produces an extract with higher concentrations of most compounds compared to the extraction using 95% ethanol only. Moreover, the process of this example using only 95% ethanol does not extract compounds in measurable amounts that are prominent in the chromatogram of Example 1 and FIG. 1 at retention times 3.08, 3.989, 6.891, 9.003, 6.536–13.547 and 20.992, respectively. Corresponding peaks are not found in the chromatogram of Example 2 and FIG. 2.

Example 3

Figure 3:
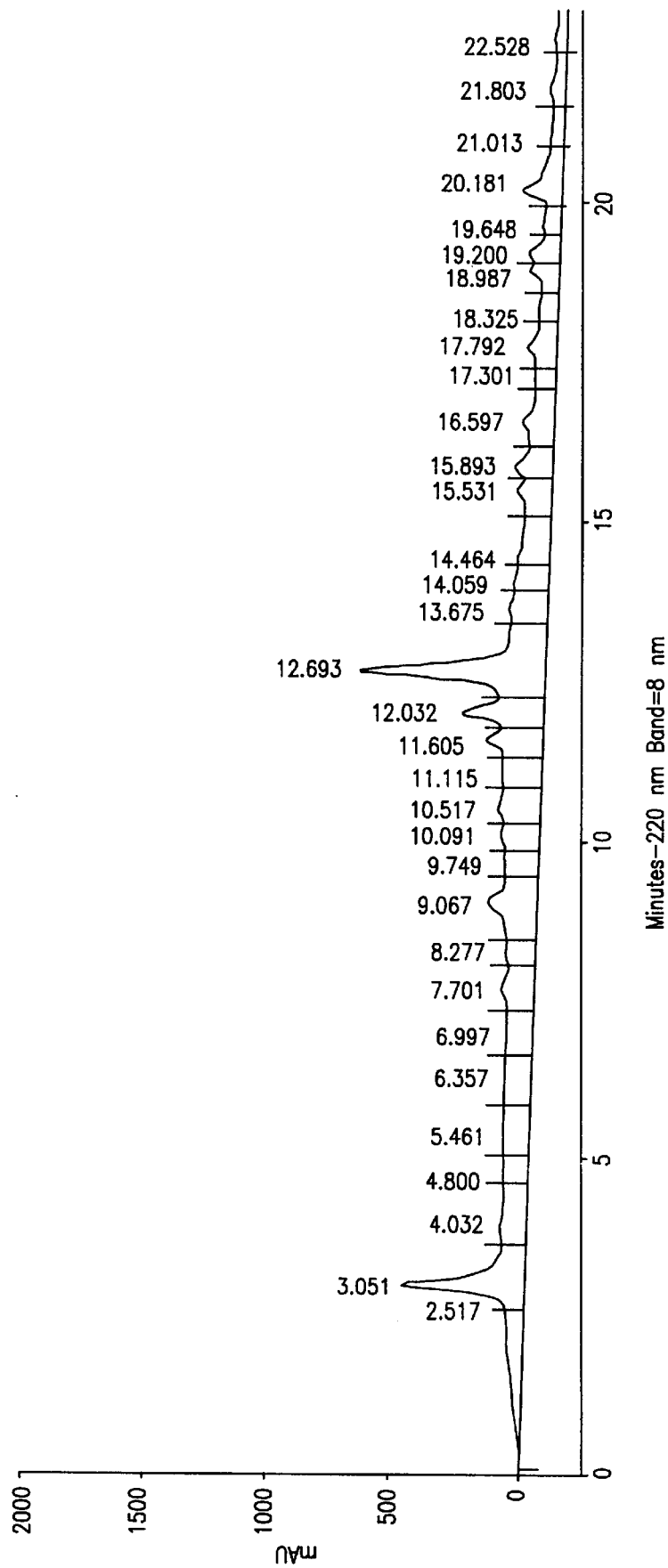
FIG. 3 is a chromatogram of the extract obtained using a 50% aqueous ethanol solvent.

The extraction process of Example 1 was carried out on *Centipeda cunninghami* except that the process used only 50% aqueous-ethanol as the extracting solvent. The resulting extract was assayed using HPLC. The chromatogram is shown in FIG. 3 and the numerical results are shown in Table 3.

TABLE 3

| Peak # | RT | AREA | AREA % | HEIGHT |
|---|---|---|---|---|
| — | 0.470 | 0 | 0.00 | 0 |
| 1 | 2.517 | 6427148 | 3.85 | 75175 |
| 2 | 3.051 | 11419865 | 6.83 | 497925 |
| 3 | 4.032 | 6091550 | 3.64 | 110024 |
| 4 | 4.800 | 2619780 | 1.57 | 102363 |
| 5 | 5.461 | 5025493 | 3.01 | 107121 |
| 6 | 6.357 | 5205257 | 3.11 | 110819 |
| 7 | 6.997 | 4710638 | 2.82 | 118100 |
| 8 | 7.701 | 5276227 | 3.16 | 139211 |
| 9 | 8.277 | 2987540 | 1.79 | 124897 |
| 10 | 9.067 | 9169545 | 5.49 | 207140 |
| 11 | 9.749 | 3457967 | 2.07 | 144429 |
| 12 | 10.091 | 3993614 | 2.39 | 164562 |
| 13 | 10.517 | 5710790 | 3.42 | 178261 |
| 14 | 11.115 | 4641255 | 2.78 | 167718 |
| 15 | 11.605 | 5425026 | 3.25 | 239021 |
| 16 | 12.032 | 6732870 | 4.03 | 336967 |
| 17 | 12.693 | 21057502 | 12.60 | 750917 |
| 18 | 13.675 | 4610416 | 2.76 | 159702 |
| 19 | 14.059 | 3069560 | 1.84 | 141273 |
| 20 | 14.464 | 5400880 | 3.23 | 128941 |
| 21 | 15.531 | 4293345 | 2.57 | 143142 |
| 22 | 15.893 | 3626786 | 2.17 | 150874 |
| 23 | 16.597 | 5459294 | 3.27 | 129126 |
| 24 | 17.301 | 1551753 | 0.93 | 81843 |
| 25 | 17.792 | 3803724 | 2.28 | 112987 |
| 26 | 18.325 | 1884669 | 1.13 | 74749 |
| 27 | 18.987 | 2371959 | 1.42 | 112294 |
| 28 | 19.200 | 2335396 | 1.40 | 119269 |
| 29 | 19.648 | 1709117 | 1.02 | 70108 |
| 30 | 20.181 | 4857363 | 2.91 | 157559 |
| 31 | 21.013 | 1716854 | 1.03 | 55027 |
| 32 | 21.803 | 2336416 | 1.40 | 62504 |
| 33 | 22.528 | 1713548 | 1.03 | 44963 |
| 34 | 23.488 | 2213130 | 1.32 | 75598 |
| 35 | 24.107 | 597073 | 0.36 | 29918 |
| 36 | 24.533 | 2324024 | 1.39 | 35781 |
| 37 | 26.901 | 250734 | 0.15 | 7889 |
| 38 | 29.461 | 1049617 | 0.63 | 25123 |

The HPLC chromatogram demonstrates that the sequential extraction process of Example 1 using solvents of varying ethanol concentrations produces an extract having compounds not found in extracts obtained using a single solvent system of 95% ethanol. Comparing the chromatogram of FIG. 3 with the chromatogram of FIG. 1 shows that the extraction process of Example 3 using only 95% ethanol recovers fewer compounds and recovers compounds in smaller concentrations than with a multi-step process using varying concentrations.

Example 4

The collected extract of Example 1 was adjusted with 20% aqueous ethanol and about 3% by volume glycerin to obtain a solution with about 0.2% by weight of total sesquiterpene lactones calculated as Brevilin A based on the HPLC chromatogram.

The resulting solution was applied topically to the skin of three adult subjects inflicted with psoriasis. After about 2 to 3 weeks of daily applications to the affected areas, the subjects reported significant reduction in the itching and dry skin commonly associated with psoriasis.

Example 5

The extract of Example 1 was used to treat chemically induced erythemal response (antiinflammatory) in 5 human subjects.

The same number of human subjects were treated with a blank containing only a vehicle. The subjects treated with the extract of Example 1 demonstrated significant response ($P<0.05$) compared to the blank. The results using the extract of Example 1 were comparable to a treatment using 1% hyaluronic acid.

Example 6

The extract of Example 1 was evaluated by standard sun protection factor assay for sunscreen efficacy. The extract showed as high as SPF 2 and an average of SPF 1.6 indicating some effects as a sunscreen. The extract was applied to five human subjects and showed increased sun protection.

Example 7

The extract of Example 1 evaluated on 5 human subjects using Dansyl chloride dye test for cell renewal properties. The tests showed a very distinct and significant response.

While advantageous embodiments have been chosen to demonstrate the invention, it will be understood by those skilled in the art that various changes and modifications can be made therein without departing from the scope of the invention as defined in the appended claims.

What is claimed is:

1. A process for obtaining a plant extract comprising the steps of
   providing a plant material of the Centipeda genus in powder form,
   sequentially macerating and extracting said plant material with a plurality of aqueous-ethanolic solvents and obtaining an extract solution of each of said solvents, wherein each sequential extraction solvent has a different ethanol concentration, and wherein said solvents have an ethanol concentration ranging from about 80% by volume to 20% by volume, and
   combining said extract solutions to obtain a plant extract.
2. The process of claim 1, wherein said Centipeda plant material is selected from the group consisting of *Centipeda cunninghami, Centipeda thespidioides,* and *Centipeda minima.*
3. The process of claim 1, further comprising drying said plant material prior to said extracting step.
4. The process of claim 1, further comprising the step of filtering said combined extract solutions for removing solid materials.
5. The process of claim 1, wherein said combined extract solutions comprise a holistically balanced concentration of constituents in said plant material.
6. The process of claim 1, wherein said macerating and extracting step comprises
   sequentially extracting said plant material with 80%, 60%, 40% and 20% by volume aqueous ethanol solutions, respectively, and obtaining an extract solution corresponding to each aqueous ethanol solution, and combining said extract solutions to obtain said extract.

7. The process of claim 1 comprising extracting said plant material with said solvents substantially at room temperature.

8. The process of claim 1, wherein said plant material is ground to about 4 mesh prior to said macerating and extracting step.

9. A holistically balanced extract of *Centipeda cunninghami*, wherein said extract is produced by the process comprising the steps of providing a *Centipeda cunninghami* plant material in powdered form, sequentially macerating and extracting said plant material with a plurality of ethanolic solvents and obtaining a plurality of extract solutions wherein each of said ethanolic solvents has a different ethanol concentration and have an ethanol concentration ranging from about 80% by volume to about 20% by volume, and combining said extract solutions to obtain said holistically balanced extract, and adding an effective amount of glycerol to prevent precipitation of compounds from said extract solution.

10. The extract of claim 9, further comprising drying said plant material prior to said extracting step.

11. The extract of claim 9, further comprising the step of filtering said combined extract solutions for removing solid materials.

12. The extract of claim 9, wherein said contacting and extracting step comprises sequentially extracting said plant material with 80%, 60%, 40% and 20% by volume aqueous ethanol solutions, respectively, and obtaining an extraction solution for each aqueous ethanol solution, and combining said extraction solutions to obtain said extract.

13. The extract of claim 9 comprising extracting said plant material with said solvents substantially at room temperature.

14. The extract of claim 9, wherein said plant material is ground to about 4 mesh prior to said contacting and extracting step.

15. The extract of claim 9, wherein said extract comprises Brevilin A, Arnicolide, Arnicolide B, Arnicolide C, Caryophyllane-2, 6-Beta-oxide, Florilenalin-angelate, Florilenalin-isobutyrate, Florilenalin-isovalerate, Helenalin, Microhelenalin B, Plenolin, 6-0-angeloyl, Plenolin, 6-0-senecoyl, Plenolin, isobutyroyl, Aurantiamide acetate, Apigenin, (cis) Chrysanthenyl acetate, Kaempferol-7-glucosyl-rhamnoside, Lupeol acetate, Quercetin, Scoparol, Beta-sitosterol, Taraxasterol, Thymol, 10-Isobutyryl-oxy-8, 9-epoxy-isobutyrate, and 9-epi Hardwickiic acid.

16. A pharmacological composition for topically treating skin disorders comprising an effective amount of a holistically balanced extract from *Centipeda cunninghami* in a pharmacologically suitable vehicle. wherein said extract is obtained by the process comprising the steps of providing a *Centipeda cunninghami* plant material in powdered form, sequentially macerating and extracting said plant material with a plurality of ethanolic solvents wherein each sequential extraction solvent has a different ethanol concentration in water and said solvents have an ethanol concentration ranging from about 80% by volume to about 20% by volume, and obtaining a plurality of extract solutions, and combining said extract solutions to produce said holistically balanced extract.

17. The composition of claim 16, wherein said extract comprises Brevilin A, Arnicolide, Arnicolide B, Arnicolide C, Caryophyllane-2, 6-Beta-oxide, Florilenalin-angelate, Florilenalin-isobutyrate, Florilenalin-isovalerate, Helenalin, Microhelenalin B, Plenolin, 6-0-angeloyl, Plenolin, 6-0-senecoyl, Plenolin, isobutyroyl, Aurantiamide acetate, Apigenin, (cis) Chrysanthenyl acetate, Kaempferol-7-glucosyl-rhamnoside, Lupeol acetate, Quercetin, Scoparol, Beta-sitosterol, Taraxasterol, Thymol, 10-Isobutyryl-oxy-8, 9-epoxy-isobutyrate, and 9-epi Hardwickiic acid.

18. The composition of claim 16, further comprising drying said plant material prior to said extracting step.

19. The process of claim 16, further comprising the step of filtering said combined extract solutions to remove solid materials.

20. The composition of claim 16, wherein said macerating and extracting step comprises sequentially extracting said plant material with 80%, 60%, 40% and 20% by volume aqueous-ethanol solutions, respectively, and collecting the extraction solutions for each of said aqueous-ethanol solutions, and combining said extraction solutions.

21. A process for treating certain skin disorders of a subject in need thereof comprising the step of topically applying a pharmacologically effective amount of a preparation to an affected skin area, wherein said preparation comprises a holistically balanced extract of *Centipeda cunninghami* in a pharmacologically acceptable vehicle, wherein said extract is obtained by a process comprising the steps of providing a *Centipeda cunninghami* plant material in granular form, sequentially macerating and extracting said plant material with a plurality of ethanolic solvents, wherein each sequential extraction solvent has a different ethanol concentration and each said ethanolic solvents having an ethanol concentration ranging from about 80% by volume to about 20% by volume, and obtaining a plurality of extract solutions, and combining said extract solutions and adding an effective amount of glycerol to prevent precipitation of compounds from solution.

22. The process of claim 21, wherein said process is for the treatment of inflammation.

23. The process of claim 21, wherein said process is for the protection from sun exposure.

24. The process of claim 21, wherein said process is for promoting skin cell renewal.

25. The process of claim 22, further comprising drying said plant material prior to said extracting step.

26. The process of claim 22, wherein said contacting and extracting step comprises sequentially extracting said plant material with 80%, 60%, 40% and 20% by volume aqueous ethanol solutions, respectively, and collecting and combining the extraction solutions to obtain said extract.

27. The process of claim 22, comprising extracting said plant material with said solvents substantially at room temperature.

28. The process of claim 22, wherein said plant material is ground to about 4 mesh prior to said extracting step.

29. The process of claim 22, wherein said extract comprises an ethanolic solution of Brevilin A, Arnicolide, Arnicolide B, Arnicolide C, Caryophyllane-2, 6-Beta-oxide, Florilenalin-angelate, Florilenalin-isobutyrate, Florilenalin-isovalerate, Helenalin, Microhelenalin B, Plenolin, 6-0-angeloyl, Plenolin, 6-0-senecoyl, Plenolin, isobutyroyl, Aurantiamide acetate, Apigenin, (cis) Chrysanthenyl acetate, Kaempferol-7-glucosyl-rhamnoside, Lupeol acetate, Quercetin, Scoparol, Beta-sitosterol, Taraxasterol, Thymol, 10-Isobutyryl-oxy-8, 9-epoxy-isobutyrate, and 9-epi Hardwickiic acid and an effective amount of glycerol to prevent precipitation of said compounds from solution.

30. The process of claim 1, wherein said extract contains at least 0.2% by weight sesquiterpene lactones.

31. The extract of claim 9, wherein said extract contains at least 0.2% by weight sesquiterpene lactones.

32. The composition of claim 16, wherein said extract contains at least 0.2% by weight sesquiterpene lactones.

33. The composition of claim 16, wherein said composition comprises about 1.0% to about 5.0% by weight of said extract.

34. The process of claim 21, wherein said extract contains at least 0.2% by weight sesquiterpene lactones.

35. The process of claim 34, wherein said preparation comprises about 1.0 to about 5.0 by weight of said extract.

36. A process for treating skin inflammation, protection from sun exposure, or promoting skin cell renewal of a subject in need thereof comprising the step of topically applying a pharmacologically effective amount of a preparation to an affected skin area, wherein said preparation comprises a holistically balanced extract of *Centipeda cunninghami* in a pharmacologically acceptable vehicle.

37. The process of claim 36, wherein said extract comprises a solution of Brevilin A, Arnicolide, Arnicolide B, Arnicolide C, Caryophyllane-2, 6-Beta-oxide, Florilenalin-angelate, Florilenalin-isobutyrate, Florilenalin-isovalerate, Helenalin, Microhelenalin B. Plenolin, 6-0-angeloyl, Plenolin, 6-0-senecoyl, Plenolin, isobutyroyl, Aurantiamide acetate, Apigenin, (cis) Chrysanthenyl acetate, Kaempferol-7-glucosyl-rhamnoside, Lupeol acetate, Quercetin, Scoparol, Beta-sitosterol, Taraxasterol, Thymol, 10-Isobutyryl-oxy-8, 9-epoxy-isobutyrate, and 9-epi Hardwickiic acid and an effective amount of glycerol to prevent precipitation of compounds from solution.

* * * * *